US009254186B2

(12) United States Patent
Landry et al.

(10) Patent No.: US 9,254,186 B2
(45) Date of Patent: Feb. 9, 2016

(54) ANCHOR FOR BONE AND SOFT TISSUE

(71) Applicant: SpineSmith Partners, L.P., Austin, TX (US)

(72) Inventors: Michael Landry, Austin, TX (US); Kevin Dunworth, Austin, TX (US)

(73) Assignee: SpineSmith Partners, L.P., Austin, TX (US)

( * ) Notice: Subject to any disclaimer, the term of this patent is extended or adjusted under 35 U.S.C. 154(b) by 0 days.

(21) Appl. No.: 14/061,585

(22) Filed: Oct. 23, 2013

(65) Prior Publication Data

US 2014/0114412 A1    Apr. 24, 2014

Related U.S. Application Data

(60) Provisional application No. 61/717,519, filed on Oct. 23, 2012.

(51) Int. Cl.
*A61F 2/08* (2006.01)

(52) U.S. Cl.
CPC ....... *A61F 2/0811* (2013.01); *A61F 2002/0835* (2013.01); *A61F 2002/0864* (2013.01); *A61F 2002/0882* (2013.01)

(58) Field of Classification Search
CPC . A61F 2002/0864; A61F 2/0829; A61F 2/08; A61F 2/0811; A61F 2002/30436; A61B 17/0401; A61B 17/0642
USPC ..................... 623/13.14, 2.36, 2.38
See application file for complete search history.

(56) References Cited

U.S. PATENT DOCUMENTS

2010/0274356 A1* 10/2010 Fening et al. ............... 623/13.14
2012/0053680 A1* 3/2012 Bolling et al. ............... 623/2.11

* cited by examiner

*Primary Examiner* — Thomas J Sweet
*Assistant Examiner* — Wade P Schutte
(74) *Attorney, Agent, or Firm* — Winstead PC

(57) ABSTRACT

The invention is directed to an anchor for fixing a tendon or a ligament in a bone comprising: an elongated tubular body having a bore extending along a longitudinal axis, said tubular body comprising first and second independent parts slidably contacting each other, the first and second independent parts each having an outer circumferential surface along a length thereof parallel to the longitudinal axis, and each having an elongated partial inner bore, such that the tubular body is capable of mounting a tendon or ligament within the partial inner bore.

8 Claims, 3 Drawing Sheets

ANCHOR FOR BONE AND SOFT TISSUE

CROSS-REFERENCES TO RELATED APPLICATIONS

This Application claims the benefit under 35 U.S.C. §119 (e) of U.S. Provisional Patent Application No. 61/717,519 filed Oct. 23, 2012 which is incorporated herein by reference in its entirety as if fully set forth herein.

BACKGROUND OF THE INVENTION

In the human anatomy, various soft tissue portions are interconnected with various bony portions. For example, a tendon may interconnect a selected muscle group with a selected portion of the anatomy. Similarly, a ligament may interconnect two bony portions. For example, the anterior cruciate ligament interconnects a portion of the tibia with a portion of the femur. Although the natural and healthy anatomy generally is able to support the various portions of the anatomy with the natural ligaments and tendons, and other selected soft tissues, injury, age, or other circumstances may cause weakening or breaking of various soft tissue portions.

For example, a strain, other injury, or disease may weaken various soft tissue portions, such as the anterior cruciate ligament (ACL). The breaking or weakening of the tissue may require the tissue to be reconnected or replaced with various autografts or xenografts that may be made of natural or synthetic materials. These various materials are generally interconnected with selected portions of the anatomy using screws or other similar friction or obstruction holding devices.

Generally, the screws or the obstruction devices must be driven into the selected bony portion to hold the selected soft tissue in the appropriate location. The procedure must be planned and executed in a precise manner to ensure that appropriate fixation of the soft tissue to the selected bony portion. Therefore, it is desirable to provide an instrument and method that allows for a substantially quick implantation or connection of a selected soft tissue graft or soft tissue portion to a selected bony portion.

SUMMARY OF THE INVENTION

The invention is directed to an anchor for fixing a tendon or a ligament in a bone comprising: an elongated tubular body having a bore extending along a longitudinal axis, said tubular body comprising first and second independent parts slidably contacting each other, the first and second independent parts each having an outer circumferential surface along a length thereof parallel to the longitudinal axis, and each having an elongated partial inner bore, such that the tubular body is capable of mounting a tendon or ligament within the partial inner bore.

DETAILED DESCRIPTION OF EXEMPLARY EMBODIMENTS

The claimed invention is directed to an anchor for fixing a tendon or a ligament in a bone comprising: an elongated tubular body having a central bore extending along a longitudinal axis, said tubular body comprising first and second independent parts slidably contacting each other, the first and second independent parts each having an outer circumferential surface along a length thereof parallel to the longitudinal axis, and each having an elongated partial inner bore, such that the tubular body is capable of mounting a tendon or ligament within the partial inner bore of said first and second independent parts.

Another embodiment of the invention is directed to a method for anchoring a tendon or ligament in a bone comprising the steps of: providing an elongated tubular body having a central bore extending along a longitudinal axis, said tubular body comprising first and second independent parts slidably contacting each other, the first and second independent parts each having an outer circumferential surface along a length thereof parallel to the longitudinal axis, and each having an elongated partial inner bore; inserting one or more tendons or ligaments into the elongated partial inner bore of said first and second independent parts; inserting a pin into the central bore of the tubular body and expanding the diameter of the central bore; and anchoring the tendon or ligament in a bone.

The claimed invention as shown and described is an anchor device that is most suited for the attachment of autograft tendons harvested from the hamstring and used to repair a torn Anterior Cruciate Ligament (ACL) in the knee. The claimed invention can be used in any application where two tissues needed to be anchored together in a cavity.

The ACL is made up of two parts, the Anterior Medial (AM) bundle and the Posterior Lateral (PL) bundle. Using an autograft hamstring to replace the ACL is typically done by taking two grafts and doubling them over so that 4 sections of tendon are used to replace the ACL. The claimed invention is directed to securing those tendons to bone using an open, expanding wire-form structure.

In an embodiment of the invention, the anchor comprises two separate patterns, each of which is repeated at multiple levels. The repetition of the two patterns at every level forms an intercalating coil-like structure that forms the anchor device of the claimed invention.

Figure 1C:
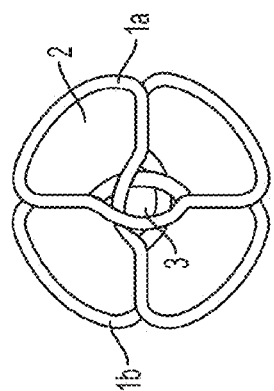
FIGS. 1A to 1E show several views an anchor device in accordance with an embodiment of the invention.
Figure 1B:
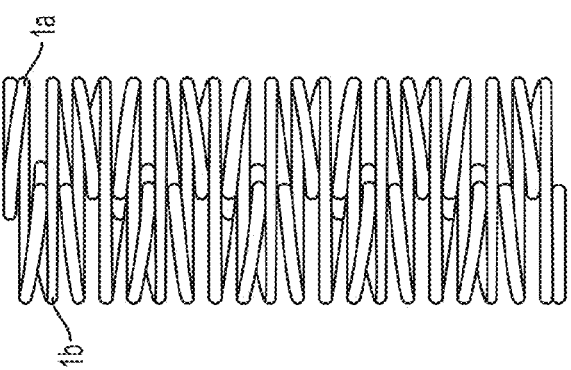
Figure 1A:
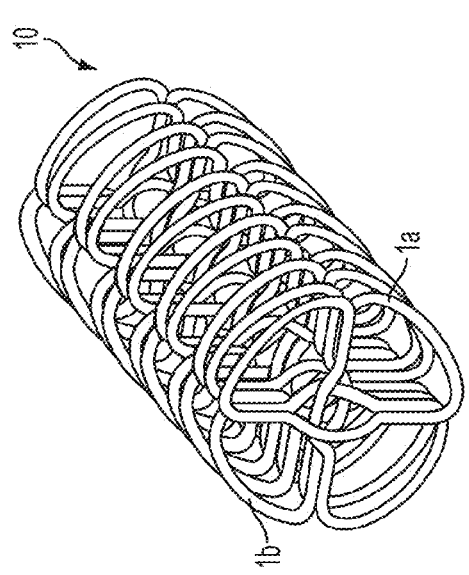

FIGS. 1A to 1C show an embodiment of the anchor as set for herein. As seen in FIG. 1A, the anchor 10 comprises an expanding wire-form structure that is made of a first independent part 1a and a second independent part 1b that slidably contact with one another. This is seen in FIG. 1B which shows a side view of anchor and the contacting of the first and second independent parts (1a and 1b). FIG. 1C shows a top view of the anchor 10 of the claimed invention. The expanding wire-form structure of the anchor 10 comprises a plurality of openings 2, through which a tendon can be inserted as shown in FIG. 2.

Figure 1D:
Figure 1E:
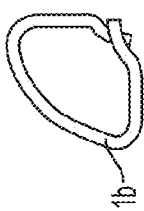

The anchor 10 comprises two separate patterns as seen in 1a and 1b, each of which is repeated at multiple levels. FIG. 1E shows the pattern of part 1a and FIG. 1D shows the pattern of part 1b. The repetition of the two patterns at multiple level forms an intercalating coil-like structure that forms the anchor device.

Figure 2:
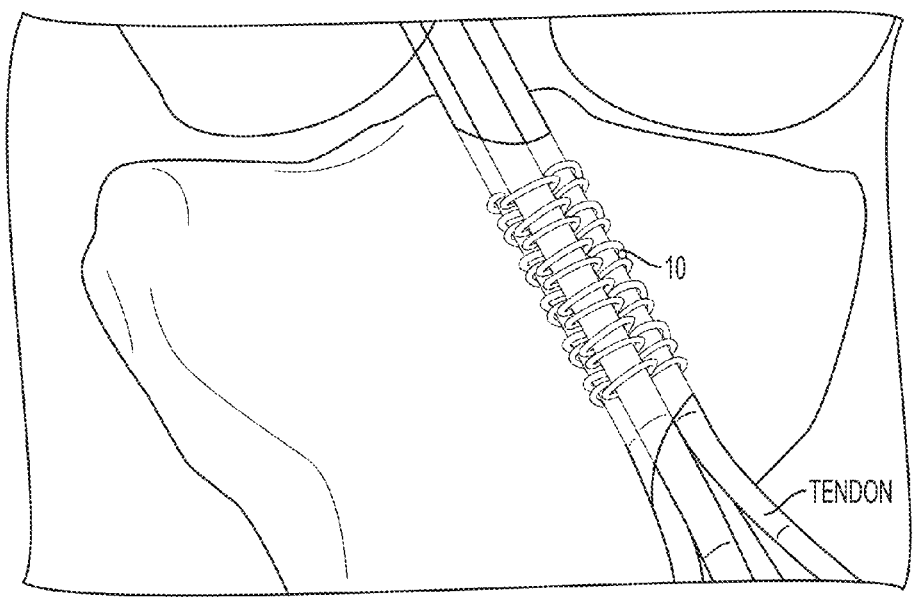
FIG. 2 shows the anchor device in use in accordance with an embodiment of the invention.

FIG. 2 shows an embodiment of the invention, where the autograft tendons are fixed to the femur and the four ends protrude from the tibia. In the next step, the 4 tendons are inserted into the 4 openings in the device (as depicted in FIG.

2) and the device is pushed into the bone. Once secure, the tendons are tensioned and oriented properly.

Figure 3A:
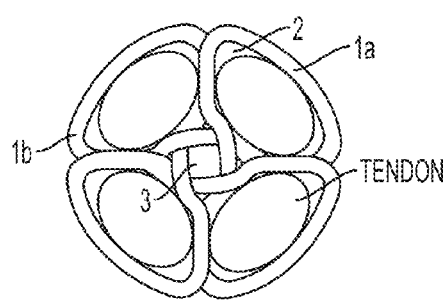
FIG. 3A and 3B show cross-sectional views of the anchor device in use in accordance with an embodiment of the invention.
Figure 3B:
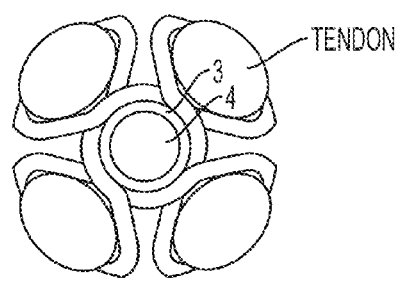

In an embodiment of the invention, a pin 4 is inserted through the core 3 of the anchor 10 while maintaining tension on the tendons. This is seen in FIGS. 3A and 3B. FIG. 3A shows the placement of tendons in each of the openings 2 of the anchor 10.

When the pin 4 is inserted into the core 3 of the anchor, the core 3 of the anchor expands, which causes several events to occur. The outer diameter of the anchor 10 expands and the wire-form structure pushes into the bone. Locally, the bone compresses and locks the anchor in place. The openings/chambers 2 housing the tendons decrease in surface areas tightening in on each of the tendons from all directions simultaneously. This causes the tendons to move radially outward, toward the bone and become compressed against the bone. The outer diameter of the anchor is loaded by the pressures from the bone, deformation of the wire and the compression of the tendons. Some portions of the wire-form structure of the anchor 10 expand more into bone than others while some areas of the wire-form structure of the anchor lock to the tendons more than expand into bone. The core 3, deformation of the wire-form structure and outward radial movement of the tendons can be seen in FIGS. 3A and 3B.

In certain embodiments of the invention, biological material is introduced into the surgical site through the anchor 10 by packing the biological material into the openings in the anchor. The biological material can be any composition that is intended to promote a biologic fusion between the tendons and the bone. For example, it can include autograft, allograft, stem cells, proteins, ceramic scaffolds, or synthetic substitutes.

Figure 4:
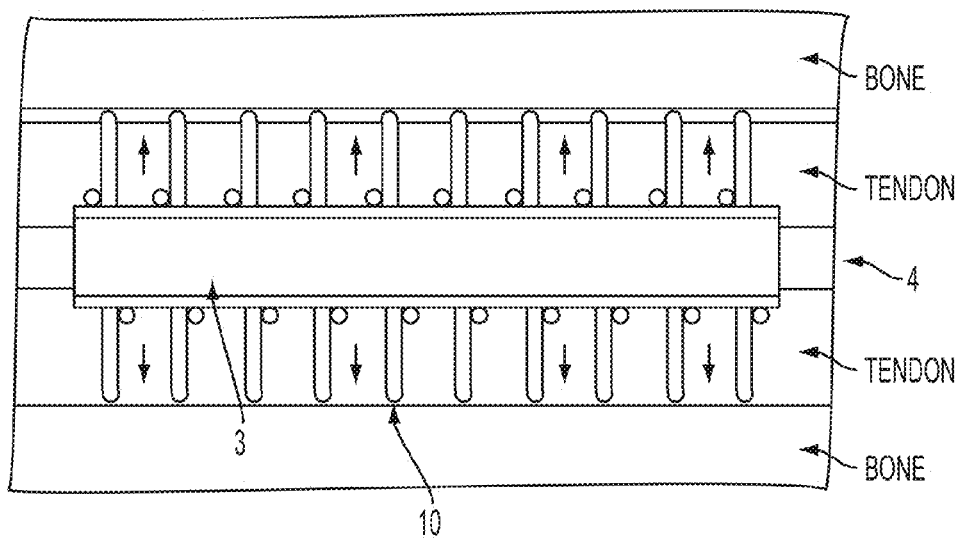
FIG. 4 shows a cross-sectional view of the anchor device in use in accordance with an embodiment of the invention.

FIG. 4 shows a longitudinal cross-section of the anchor device 10 in use in accordance with an embodiment of the invention. As is seen in FIG. 4, the tendons are housed within the openings 2 of the anchor device 10. The insertion of a pin 4 in the direction shown by the arrow, into the core 3 of the anchor 10 causes the wire-form structure to expand toward the bone, as indicated by the arrows. This causes the tendons to move radially outward, toward the bone and become compressed against the bone.

In the preceding detailed description, the invention is described with reference to specific exemplary embodiments thereof and locations of use within the spine. Various modifications and changes may be made thereto without departing from the broader spirit and scope of the invention as set forth in the claims. The specification and drawings are, accordingly, to be regarded in an illustrative rather than a restrictive sense.

What is claimed is:

1. An anchor for fixing a tendon or a ligament in a bone comprising: an elongated tubular body having a central bore extending along a longitudinal axis of the tubular body, said tubular body defined by a repeating overlap between a first wire-form pattern and a second wire-form pattern, the first and second wire-form patterns each having an elongated partial inner bore parallel to the central bore, such that the tubular body is capable of mounting a tendon or ligament within the partial inner bore of said first and second wire-form patterns.

2. The anchor of claim 1 further comprising a pin inserted into the central bore.

3. The anchor of claim 2 wherein insertion of the pin into the central bore causes an expansion of the central bore.

4. A method for anchoring a tendon or ligament in a bone comprising the steps of:
   providing an elongated tubular body having a central bore extending along a longitudinal axis, said tubular body defined by a repeating overlap between a first wire-form pattern and a second wire-form pattern the first and second wire-form patterns each having an elongated partial inner bore parallel to the central bore;
   inserting one or more tendons or ligaments into the elongated partial inner bore of said first and second wire-form patterns;
   inserting a pin into the central bore of the tubular body and expanding the diameter of the central bore; and
   anchoring the tendon or ligament in a bone.

5. The anchor of claim 1, wherein the first wire-form pattern comprises a repeating first shape and the second wire-form pattern comprises a repeating second shape.

6. The anchor of claim 2, wherein the elongated partial inner bores of the first and second wire-form patterns decrease in surface area in response to the insertion of the pin.

7. The anchor of claim 2, wherein a circumference of the tubular body increases in response to the insertion of the pin.

8. The method of claim 4, wherein inserting the pin decreases a surface area of the elongated partial inner bores of the first and second wire-form patterns.

* * * * *